(12) United States Patent
Brugner

(10) Patent No.: US 7,748,577 B2
(45) Date of Patent: Jul. 6, 2010

(54) CARTRIDGE PISTON

(75) Inventor: Nikolaus Brugner, Ziemetshausen (DE)

(73) Assignee: Sülzer Chemtech AG, Winterthur (CH)

( * ) Notice: Subject to any disclaimer, the term of this patent is extended or adjusted under 35 U.S.C. 154(b) by 408 days.

(21) Appl. No.: 11/973,434

(22) Filed: Oct. 9, 2007

(65) Prior Publication Data
US 2008/0083789 A1   Apr. 10, 2008

(30) Foreign Application Priority Data
Oct. 6, 2006   (DE) .................. 10 2006 047 289

(51) Int. Cl.
*G01F 11/00* (2006.01)
(52) U.S. Cl. .................. 222/387; 222/326; 222/386
(58) Field of Classification Search .............. 222/386, 222/326, 387
See application file for complete search history.

(56) References Cited

U.S. PATENT DOCUMENTS

| | | | | |
|---|---|---|---|---|
| 5,042,695 | A * | 8/1991 | Battegazzore | 222/259 |
| 5,178,305 | A * | 1/1993 | Keller | 222/386 |
| 5,301,839 | A * | 4/1994 | Eierle et al. | 222/95 |
| 5,400,926 | A * | 3/1995 | Keller | 222/327 |
| 6,494,348 | B2 * | 12/2002 | Prestele | 222/326 |
| 6,598,766 | B1 * | 7/2003 | Brugner | 222/326 |
| 6,899,254 | B1 * | 5/2005 | Sandholm et al. | 222/387 |
| 2005/0029306 | A1 * | 2/2005 | Brennan | 222/327 |
| 2005/0066809 | A1 * | 3/2005 | Nehren et al. | 91/422 |

FOREIGN PATENT DOCUMENTS

| | | |
|---|---|---|
| DE | 297 02 551 U1 | 5/1997 |
| DE | 200 10 417 U1 | 11/2001 |
| DE | 103 42 091 A1 | 4/2005 |
| EP | 1 165 400 B1 | 1/2002 |

* cited by examiner

*Primary Examiner*—Kevin P Shaver
*Assistant Examiner*—Donnell Long
(74) *Attorney, Agent, or Firm*—Francis C. Hand; Carella, Byrne, Cecchi

(57) ABSTRACT

The cartridge piston has an outer wall, an inner support body and radial connection webs between the outer wall and the inner support body. In order to ensure a good sealing behavior under unilateral strain or asymmetric strain by a pressing plunger, a stiffening body connected to the connection webs is provided between the outer wall and the inner support body. The connection webs have a gap that extends at least up to half the height of the cartridge piston at the lower side of the cartridge piston between the outer wall and the stiffening body.

11 Claims, 2 Drawing Sheets

CARTRIDGE PISTON

This invention relates to a cartridge piston. More particularly, this invention relates to a cartridge piston used in a dispensing cartridge, such as an explusion pistols.

Various cartridge pistons have been known, for example, as described in EP 1 165 400 B1. There, radial connection webs extending in a star shaped pattern are provided between an outer wall and an inner support body of a cartridge piston of annular shape. The connection webs have lateral ribs and extend almost over the total height of the cartridge piston. As can in particular be seen from FIG. 1 of EP 1 165 400 B1, the connection webs are only slightly set back with respect to the lower end face in the region of an outwardly inclined support lip at the lower side of the cartridge piston so that a stable connection is produced between the inner annular support body and the outer wall. Cartridge pistons of this type are thus relatively stiff and can be inserted into cartridges without any larger deformations and can be displaced with the help of pressing plungers for the pressing out of material from the cartridges.

Cartridges having cartridge pistons of this type are usually used for the dispensing of the materials located in the cartridges, e.g. in expulsion pistons especially provided for this purpose. Generally, a pressing plunger acts on the cartridge piston to expel the material therein. However, particularly with low-cost expulsion pistols, the pressing plungers can move with respect to the cartridge axis so that the cartridge pistons are pressed in at one side or with a bias. This can result in sealing problems with stiff cartridge pistons.

It is the object of the invention to provide a cartridge piston of the initially named kind which ensures a good sealing behaviour on a unilateral or biased load by a pressing plunger.

It is another object of the invention to provide a cartridge piston that provides a reliable seal within a cartridge under asymmetrically applied loads.

Briefly, the invention provides a cartridge piston comprised of an outer peripheral wall; an inner support body within the outer peripheral wall and a stiffening body concentrically between the outer wall and the inner support body. In addition, the cartridge piston has radially disposed connection webs between the outer wall and the stiffening body and between the stiffening body and the inner support body. At least one of the connection webs between the outer wall and the stiffening body defines a gap extending at least up to half the height of the cartridge piston at the lower side of the cartridge piston. The cartridge piston also has a cover transverse to the outer wall and the inner support body.

The inner supporting body and the stiffening body ribbed therewith create a very stiff, i.e. rigid, piston core that can transfer the pressure of the medium within a cartridge onto a pressing plunger without deformation.

The outer wall is made with a radially outwardly projecting upper rim with a sealing edge and a radially outwardly projecting lower rim configured as a support lip. In addition, the outer wall is hingedly connected to the cover. The outer wall of the cartridge piston with the sealing or support lips is, in contrast, pivoted at the piston core in an extremely flexible manner due to the gaps in the connection webs so that the sealing and support lips can adapt in a flexible manner to a cartridge wall when the piston core is inclined at an angle when in use in a cartridge.

When the piston cartridge is caused to incline, e.g. by an eccentric pressing of a pressing plunger, the piston core can become inclined, while the outer wall adapts to the sealing and support lips of the cartridge. The sealing function of the cartridge piston can thereby be maintained even with larger inclined positions or unilateral strains on the pressing plunger.

In a particularly expedient embodiment, the gap in the connection webs converges in the shape of a wedge from the lower side of the cartridge piston towards the top. The support lip at the bottom of the cartridge is thereby also extremely flexible in the radial direction and can be biased radially more pronouncedly without generating any large frictional forces.

In a further advantageous aspect, the cartridge piston has an upwardly open marginal annular groove at its upper side. Thus, only a relatively narrow web remains between the annular groove and the gap in the connection webs towards the outer wall so that the outer wall is extremely flexibly linked to the stable cartridge core in the manner of a pivot joint.

One or more further stiffening bodies can also be arranged radially inside the stiffening body in the vicinity of the outer wall, particularly with larger cartridge pistons.

The inner support body can be of hollow cylindrical shape in an expedient embodiment and can contain a bleeding valve for the air enclosed between the filling material and the cartridge piston. The inner support body can, however, also be configured as a solid core as a starting point of the radial connection webs extending in star shape towards the outer wall.

Further special features and advantages of the invention result from the following description of preferred embodiments with reference to the drawing wherein.

Figure 1:
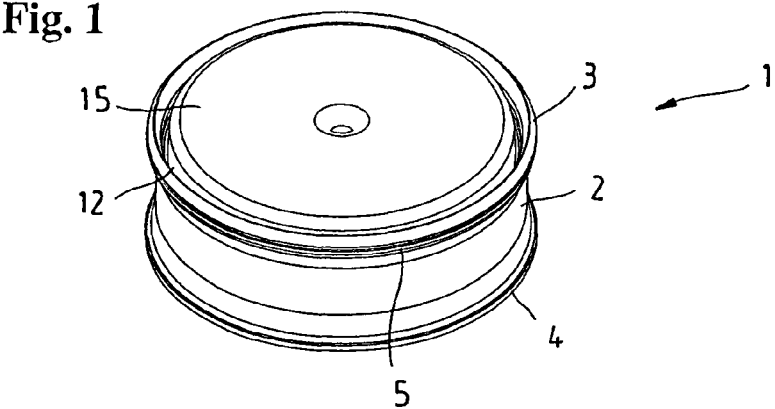
FIG. 1 illustrates a perspective view of a cartridge piston in accordance with the invention.

Referring to FIG. 1, the cartridge piston 1 is constructed for use as an expulsion piston for cartridges which are used for the storage and dispensing of different materials, such as adhesives, sealants and similar. The cartridges are as a rule used in commercial expulsion pistols for dispensing. These expulsion pistols contain a pressing plunger by which the cartridge piston 1 can be pressed into the associated cartridge and, thus, the material located in the cartridge can be expelled via a dispensing opening of the cartridge.

Figure 3:
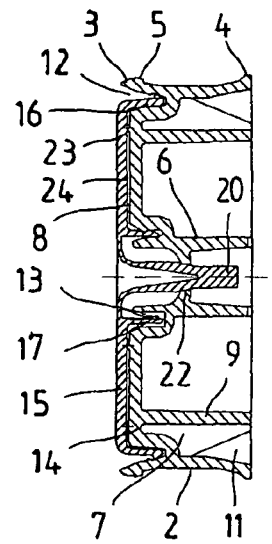
FIG. 3 illustrates a cross-sectional view along the lines A-A of FIG. 2.

Referring to FIGS. 1 and 3, the cartridge piston 1 contains an outer wall 2 having a radially outwardly projecting upper rim 3 at the upper side and one likewise radially outwardly projecting lower rim 4 at the lower side. A sealing edge 5 is shaped at the upper rim 3. A sealing lip for the sealing of the cartridge piston 1 with respect to the inner wall of a cartridge is formed by the upper rim 3 with the sealing edge 5. The lower rim 4 forms a support lip for the guidance of the cartridge piston 1 within the cartridge. The outer diameter of the lower rim 4 and of the upper rim 3 with the sealing edge 5 is larger than the inner diameter of the associated cartridge. The sealing lip and the support lip are thereby biased.

Figure 2:
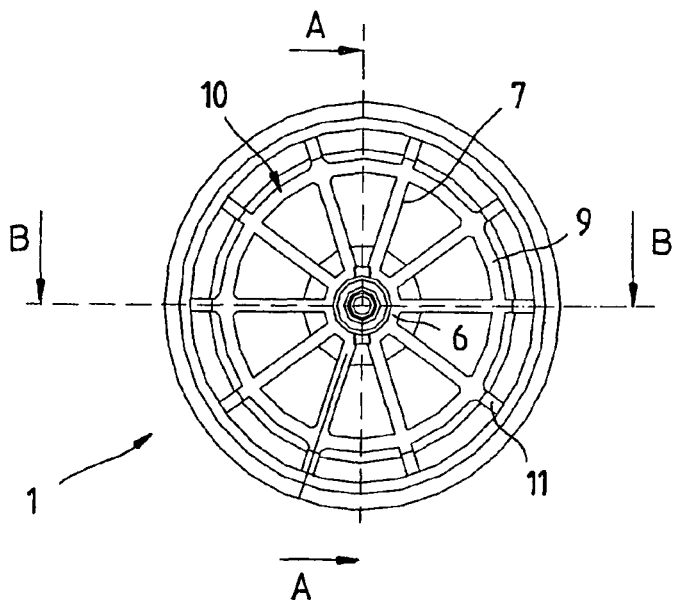
FIG. 2 illustrates a bottom view of the cartridge piston of FIG. 1.

Referring to FIGS. 2 and 3, the cartridge piston 1 has a central inner hollow cylindrical support body 6 radially and concentrically inside the outer wall 2 as well as radially disposed connection webs 7. These connection webs extend in a star shape, starting from the hollow cylindrical support body 6, toward the outer wall 2 and connect the outer wall 2 to the support body 6.

Figure 4:
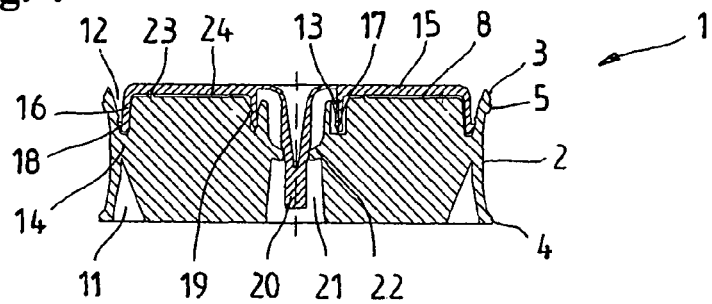
FIG. 4 illustrates a cross-sectional view along the lines B-B of FIG. 2.

Referring to FIGS. 3 and 4, the cartridge piston 2 has a cover 8 at the upper side facing towards the cartridge content that is transverse to the outer wall 2 and the inner support body 6. In addition, a stiffening body 9 connected to the connection webs 7 is provided concentrically between the inner support body 6 and the outer wall 2. In the embodiment shown, the stiffening body 9 is annular and is formed by ring segment shaped stiffening webs 10 between the connection webs 7. The stiffening webs 10 can, however, also extend in a straight line and the stiffening body 9 can be angular or have another suitable shape.

As illustrated in FIGS. 3 and 4, each connection web 7 has a gap 11 extending up to half the piston height at the lower side of the cartridge piston 1 between the stiffening body 9 and the outer wall 2. The gap 11 is made in wedge shape and converges in the direction of the upper side of the cartridge piston 1. The lower side of the stiffening body 9 terminates flush with the lower side of the outer wall 2 so that the inner part and the outer part are approximately of the same height.

As illustrated, the outer wall 2 is spaced from the cover 8 to define an annular groove 12 of V shape in cross-section and while a central portion of the cover 8 is formed with a cavity facing the cartridge content and about which an inner annular groove 13 is coaxially formed.

The outer annular groove 12 ensures that the upper rim 3 with the sealing lip 5 is laterally flexible and can contact the inner wall of a cartridge. In addition, the outer annular groove 12 ensures that the sealing lip formed by the upper rim 3 with the sealing edge 5 is pressed radially outwardly towards the wall of the cartridge by the pressure of the cartridge content acting on the cartridge piston on the pressing out of the cartridge.

The web 14 remaining between the gap 11 and the upper annular groove 12 in accordance with FIG. 4 is relatively narrow so that the outer wall 2 is extremely flexibly linked to the stable cartridge core in the manner of a pivot hinge. The outer wall 2 of the cartridge piston can thereby adapt ideally to the inner wall of the cartridge.

A cover plate 15 is secured over the cover 8 to face the interior of the cartridge. As illustrated, this cover plate 15 has peripheral downwardly angled outer rim 16 engaging into the outer annular groove 12 and an inner ring web 17 engaging into the inner annular groove 13. Latch noses 18 or latch grooves 19, shown in FIG. 4, are provided at the downwardly angled outer rim 16 and the inner ring web 17 of the cover plate 15 and the cover plate 15 is held by them via a latch connection at the cartridge piston 1.

The cover plate 15 consists e.g. of polyamide or another material resistant with respect to the cartridge content in order to thus protect the cartridge piston 2 consisting e.g. of polyethylene or another soft plastic.

As shown in FIGS. 3 and 4, a conical spigot 20 depends centrally from the cover plate 15 into a bore 21 in the support body 6 and is shaped to be axially movable relative to the support body 6. In addition, the support body 6 is formed with a radially inwardly directed annular lip 22 through which the spigot 20 passes to form a bleed valve therewith.

Interrupted spacing webs or spacing cams 23 are located on the surface of the cover 8 of the cartridge piston 2 and the cover plate 15 is held by them in spaced apart relation to the surface of the cover 8 with a predetermined small gap 24.

The conical spigot 20 is pressed in from below by a corresponding nose at a tool so that the bleeding valve opens on the insertion of the cartridge piston 2 into the cartridge. Air located in the cartridge can thereby escape via intermediate spaces between the latch noses 18 on the outer rim 16 and the annular groove 12, the gap 24 between the cover 8 and the cover plate 15, a gap between the ring groove 13 and the ring web 17 and the open bleeding valve, i.e. between the spigot 20 and lip 22.

Figure 5:
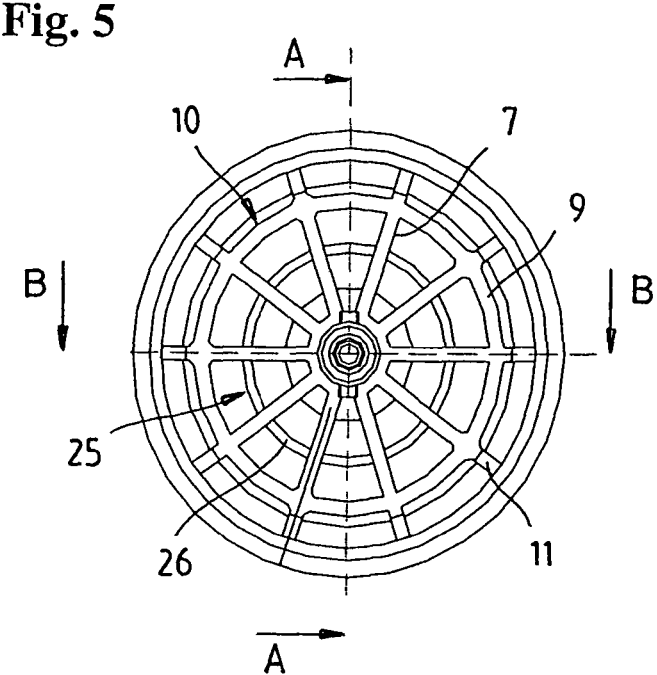
FIG. 5 illustrates a bottom view of a modified cartridge piston in accordance with the invention.
Figure 6:
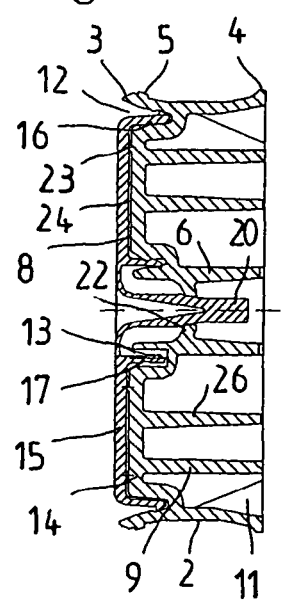
FIG. 6 illustrates a cross-sectional view along the lines A-A of FIG. 5.
Figure 7:
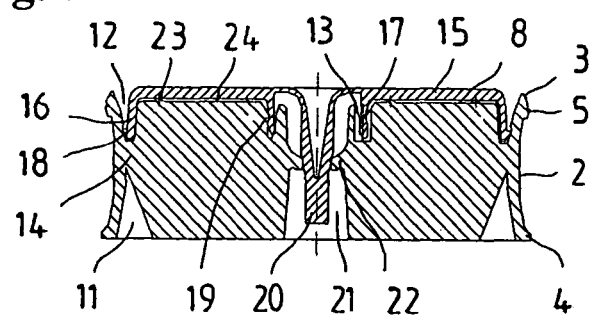
FIG. 7 illustrates a cross-sectional view along the lines B-B of FIG. 5.

Referring to FIGS. 5 to 7, wherein like reference characters indicate like parts as above, the cartridge piston is made with a further annular stiffening body 25 radially inside the annular stiffening body 9 and concentric thereto. The stiffening body 25 is also formed by ring segment shaped stiffening webs 26 between the connection webs extending in star shape. Otherwise, the cartridge piston has a construction corresponding to that of the first embodiment.

The invention thus provides a cartridge piston which ensures a good sealing behaviour in response to a unilateral or biased load by a pressing plunger and that provides a reliable seal within a cartridge under asymmetrically applied loads.

What is claimed is:

1. A cartridge piston comprising
an outer peripheral wall having a radially outwardly projecting upper rim at an upper side for forming a sealing lip to engage a wall of a cartridge, and a radially outwardly projecting lower rim at a lower side for forming a support lip for guiding the piston within the cartridge;
an inner support body within said outer peripheral wall of predetermined height;
an annular stiffening body concentrically between said outer wall and said inner support body, said stiffening body being of a height equal to said predetermined height of said inner support body and having a lower side flush with the lower side of said lower rim;
radially disposed connection webs between said outer wall and said stiffening body and between said stiffening body and said inner support body, at least one of said connection webs between said outer wall and said stiffening body defining a gap extending at least up to half the height of the cartridge piston at the lower side of the cartridge piston; and
a cover transverse to said outer peripheral wall and said inner support body, said upper rim of said outer peripheral wall being spaced from said cover to define an annular groove therebetween of V-shaped cross-section.

2. A cartridge piston in accordance with claim 1 wherein said gap converges upwardly in wedge shape from the lower side of the cartridge piston.

3. A cartridge piston in accordance with claim 1 further comprising a cover plate disposed over said cover.

4. A cartridge piston in accordance with claim 3 further comprising a radially inwardly directed annular lip on said support body and a conical spigot depending from said cover plate and projecting through said annular lip to form a bleed valve therewith.

5. A cartridge piston in accordance with claim 3 further comprising a plurality of spacers on said cover for spacing said cover plate from said cover with a predetermined small gap.

6. A cartridge piston in accordance with claim 1 further comprising a second stiffening body arranged between said first stiffening body and said support body.

7. A cartridge piston comprising
a cover of annular shape;
an outer peripheral wall extending from said cover and having a radially outwardly projecting upper rim at an upper side for forming a sealing lip to engage a wall of a cartridge, and a radially outwardly projecting lower rim at a lower side for forming a support lip for guiding the piston within the cartridge; said upper rim being spaced from said cover to define an annular groove therebetween of V-shaped cross-section.

an inner support body extending from said cover concentrically within said outer peripheral wall and being of predetermined height;

an annular stiffening body extending from said cover concentrically between said outer wall and said inner support body, said stiffening body being of a height equal to said predetermined height of said inner support body and having a lower side flush with the lower side of said lower rim;

a first array of radially disposed connection webs between said outer wall and said stiffening body, at least some of said connection webs defining a gap relative to said lower rim of said outer wall and extending at least up to half the height of the cartridge piston at the lower side of the cartridge piston whereby said lower rim of said outer wall is hingedly connected to said cover to pivot relative to said cover; and a second array of radially disposed connection webs connected to and between said stiffening body and said inner support body to form a rigid core for transferring a force therethrough.

8. A cartridge piston as set forth in claim 7 further comprising a cover plate disposed over said cover and having a peripheral outer rim engaged in said annular groove.

9. A cartridge piston as set forth in claim 8 further comprising a radially inwardly directed annular lip on said support body and an axially movable conical spigot depending centrally from said cover plate and projecting through said annular lip to form a bleed valve therewith.

10. A cartridge piston in accordance with claim 9 further comprising a plurality of spacers on said cover for spacing said cover plate from said cover with a predetermined small gap to define a path for air from within a cartridge through said gap and said bleed valve.

11. In combination a cartridge having a predetermined inner diameter; and a piston slidably disposed in said cartridge, said piston having an outer peripheral wall having a radially outwardly projecting upper rim at an upper side for forming a sealing lip of larger diameter than said inner diameter of said cartridge to engage a wall of said cartridge, and a radially outwardly projecting lower rim at a lower side for forming a support lip of larger diameter than said inner diameter of said cartridge for guiding the piston within said cartridge; an inner support body within said outer peripheral wall of predetermined height; an annular stiffening body concentrically between said outer wall and said inner support body, said stiffening body being of a height equal to said predetermined height of said inner support body and having a lower side flush with the lower side of said lower rim; radially disposed connection webs between said outer wall and said stiffening body and between said stiffening body and said inner support body, at least one of said connection webs between said outer wall and said stiffening body defining a gap extending at least up to half the height of the cartridge piston at the lower side of the cartridge piston; and a cover transverse to said outer peripheral wall and said inner support body, said upper rim of said outer peripheral wall being spaced from said cover to define an annular groove therebetween of V-shaped cross-section.

* * * * *